United States Patent [19]
Warshawsky et al.

[11] Patent Number: 4,652,519
[45] Date of Patent: Mar. 24, 1987

[54] BIFUNCTIONAL CHELATING AGENTS AND PROCESS FOR THEIR PRODUCTION

[75] Inventors: Abraham Warshawsky; Meir Wilchek, both of Rehovot; Janina Altman, Haifa; Nurit Shoef, Holon, all of Israel

[73] Assignee: Yeda Research and Development Company Limited, Rehovot, Israel

[21] Appl. No.: 574,613

[22] Filed: Jan. 27, 1984

[30] Foreign Application Priority Data

Feb. 3, 1983 [IL] Israel ................................. 67825
Mar. 1, 1983 [IL] Israel ................................. 68010

[51] Int. Cl.$^4$ .................. G01N 33/53; G01N 33/536; G01N 33/534
[52] U.S. Cl. .......................................... 435/7; 436/536; 436/542; 436/545; 436/804; 436/815; 436/817; 436/824; 530/350; 534/14; 556/1
[58] Field of Search ............... 436/542, 536, 545, 804, 436/815, 817, 824; 435/7; 530/350; 534/14; 556/1

[56] References Cited

U.S. PATENT DOCUMENTS 4,320,109  3/1982  Wolf et al. ..................... 436/542
4,432,907  2/1984  Wieder et al. .................. 436/547

OTHER PUBLICATIONS

Sundberg et al., J. Med. Chem., 17 (1974), 1304–7.

Primary Examiner—Christine M. Nucker
Attorney, Agent, or Firm—Browdy and Neimark

[57] ABSTRACT

There are provided bifunctional chelating agents, which are analogues of EDTA, conjugates of same with a variety of haptens and conjugates of such conjugates with haptens with certain metals, forming metal complexes. The metal complexes have a variety of uses, among these various assays for the determination of haptens and macromolecules. There is also provided a process for the production of the above. There are provided radioimmunoassays based on the above conjugates with metal cations.

4 Claims, No Drawings

BIFUNCTIONAL CHELATING AGENTS AND PROCESS FOR THEIR PRODUCTION

FIELD OF THE INVENTION

The present invention relates to novel bifunctional analogues of ethyleneddiaminetetraacetic acid, a process for their production, their conjugation to haptens, steroids, macromolecules, such as proteins, and the use of metal complexes of the conjugates in the radioimmunassay determination of such haptens and macromolecules, or in therapeutic applications.

BACKGROUND OF THE INVENTION

The attachment of bifunctional analogues of the strong metal chelating compound EDTA (ethylene diamine tetraacetic acid) by a covalent bond to biological molecules is of considerable interest, since the metal complexes of such a bifunctional chelating agent can be applied for radiolabelling of small molecules, macromolecules (antigens, antibodies), membranes, cells, in radioimmunoassays, and as tumor locating reagents.

Meares et al (M. W. Sundberg, C. F. Meares, D. A. Goodwin and C. I. Diamanti, J. Med. Chem., Vol 17, 1304, 1974) prepared 1-(p-aminophenyl) ethylenediaminetetraacetic acid (1) and bound it by diazotization to human serum albumin and bovine fibrinogen. They also used the bromoacetyl derivative bound to bleomycin as a reagent in tumor localization (Meares et al., J. Med. Chem., 22, 1019, 1979; J. Nucl. Med., 22, 787, 1981).

The big disadvantage of Meare's compound 1 is in the low and not always reproducible results, due to the sensitivity of the p-nitrophenylene diamine system, which tends to undergo, under the alkylation conditions, side reactions (W. Henhorf and C. K. Ingold, J. Chem. Soc., 1009, 1927).

Yeh, et al (S. M. Yeh, D. G. Sherman and C. F. Meares, Anal. Biochem., 100, 152, 1979) prepared a series of substituted EDTA (2) through amino acid conversion via borane reduction of amides and alkylation with bromoacetic acid. This series of compounds lacks the amino function needed for diazotization and requires additional protection of the EDTA function during the coupling process to the biological macromolecules.

Other EDTA analogues have been attached to monoclonal antibodies and used for detection of mouse erythroid tumors using a high resolution gamma camera. The chelatable radioactive metals with short half-lives, gallium-67, indium-111 and technetium-99 m are optimal for gamma camera imaging, while gallium-68 is optimum for positron emmision tomography, and scandium-47 or other alpha emitting isotopes are optimum for therapeutic effects (D. A. Scheinberg, M. Strand and O. A. Gansow, Science, 215, 1511, 1982).

The chelates tried by Scheinberg et al., included 1-(p-benzyldiazonium) EDTA (3), the p-hydroxybenzimidate of (3), 1-(p-carboxymethoxy benzyl) EDTA (4) and carboxycarbonic anhydride of DPTA diethylenetriaminepenta acetic acid) (5).

From all the EDTA analogues described above "only 4 could be conjugated to immunoglobulines in sufficient yield without large losses of biological activity" (quotation from Scheinberg et al).

Other studies in similar directions are labelling of preformed liposomes with Ga-67 and Te-99 m, using DPTA-anhydride (D. Y. Hnatowich, B. Friedman, B. Clancy and M. Novak, J. Nucl. Med., 22, 810, 1981) which was previously reported by W. C. Eckelman, S. M. Karesh and R. C. Reba, J. Pharmac. Sci., 64, 704, 1975).

Evaluation of the viability of In-111 labelled DPTA, coupled to Fibrinogen, was also reported by Hnatowich et al (W. W. Sayne, D. Y. Hnatowich, D. W. Doherty, R. L. Childs, D. Lanteigne and Y. Ansell, J. Nucl. Med. 23, 627, 1982).

The above examples show that the common approach to the synthesis of EDTA analogues has been the reduction of the appropriate nitrile or amide and subsequent alkylation.

From this lengthy introduction it can be surmised that new bifunctional chelating agents incorporating a strong metal chelating center (the EDTA type center), and a second functionality, sterically well separated from the EDTA center, which in addition are stable under the common conjugating conditions, will be of great interest for use in radioimmunoassays and for tumor imaging. The compounds described in this application are novel and correspond to those requirements.

SUMMARY OF THE INVENTION

The present invention relates to novel bifunctional chelating agents and to a novel route for their synthesis. The first phase is the synthesis of 2-substituted ethylenediamine tetraacetic acid compounds of type 6.

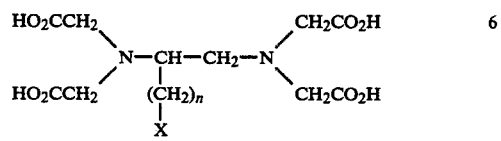

where (A) X=CO$_2$H; —NH$_2$; —CHO; HC≡N— and n=1-20 (P) X=can also be

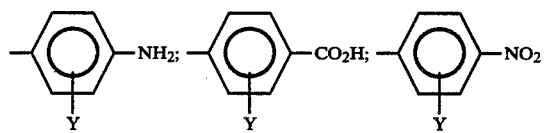

where y is an alkyl, cycloalkyl, aryl, and n=2-20.

Compounds of the type 6A are synthesized from 4-substituted imidiazoles (the 4 and 5 positions for imidazoles are identical), which undergo the Bamberger ring cleavage acylation as follows:

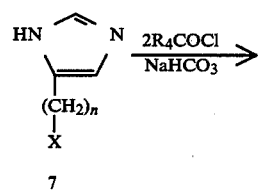

7

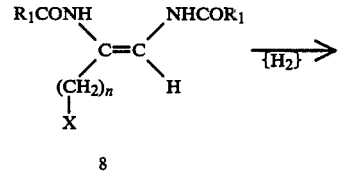

8

-continued

9 where n is an integer of 1 to 20 (preferably 1-6).
X=—CO$_2$H
X=NH$_2$
X may also designate —NHZ (where Z is p-toluenesulfonyl, benzenesulfonyl, nitrobenzenesulfonyl, aminobenzenesulfonyl, or carbo-alkoxy);
X may also be an imine (C=N— where Z is acyl, or x may be $$\overset{H}{\underset{}{(C-N=)}},$$

where Z is $$=C\begin{matrix}R_2\\R_3\end{matrix},$$

where R$_2$=R$_3$=alkyl or R$_2$=H and R$_3$=phenyl.

X may also be a benzyloxy group (and correspondingly, Z=alkyl).

R$_1$ is usually a phenyl, aryl or substituted aryl, but may also be a benzyloxy, alkoxy or acyl group.

The selection of the acylating reagent R$_1$COCl must be in harmony with the selection of the end group X, so that the ring cleavage reaction will proceed without the removal of the end group X and viceversa.

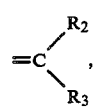

9

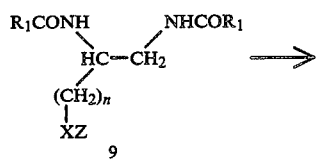

10

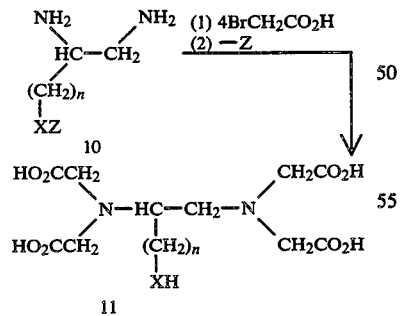

11

X = CO$_2$—; —NH—

Further demonstration of this invention is given in two specific examples, one for the case where X is an acidic function, —CO$_2$H, and the other where X is a basic function (—NH$_2$).

The synthesis of a 4,5-diamino-(N,N,N'N'-Tetraacetic acid) valeric acid (5) is described hereinafter:

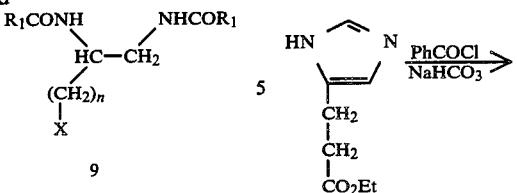

(1)

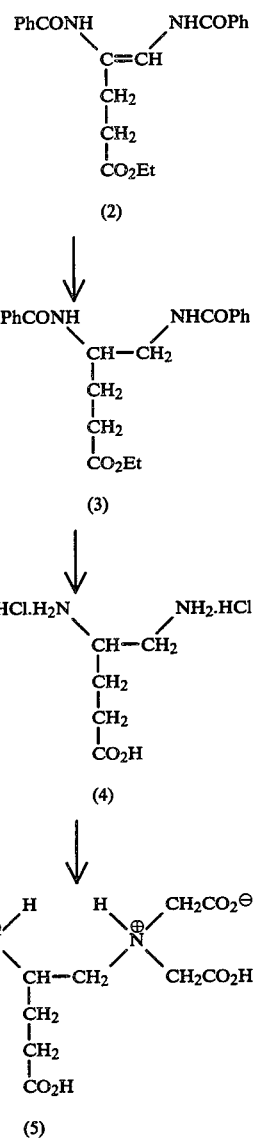

Ethyl-4-imidazole propionate (12) undergoes the Bamberger ring cleavage upon dibenzoylation to the unsaturated chain product (13), which is reduced to the diamido ester (14). Exhaustive hydrolysis of (14) with HCl yields 4,5-diaminovaleric acid dihydrochloride (15) (the previously unknown D.L.- -ornithine). Alkylation of (15) with 4 equivalents of bromoacetic acid yields 4,5-diamino-(N,N,N',N'-tetraacetic acid) valeric acid (16).

Similarly, 3,4-diamino-(N,N,N',N'-tetraacetic acid) butyric acid (17) and 7,8-diamino-(N,N,N',N'-tetraacetic acid) octanoic acid (18) are synthesized from ethyl-4-imidazole acetate (19) and ethyl-4-imidazole hexanoate (20).

As was mentioned earlier, acylation with ethyl chloroformate or benzyl chloroformate with Bamberger ring cleavage of ethyl-4-imidazole propionate (12) will yield the dicarbamate (21) which can be further transformed to (16) by the reaction sequence described above.

Similarly, acylation with ethyl chloroformate with Bamberger cleavage of ethyl-4-imidazole propionate (12) and ethyl-4-imidazole hexanoate (21), followed by the same reaction sequence, yields (22) and (23), respectively.

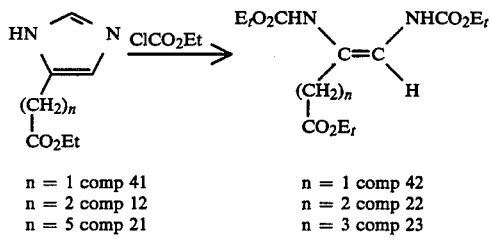

n = 1 comp 41
n = 2 comp 12
n = 5 comp 21 n = 1 comp 42
n = 2 comp 22
n = 3 comp 23

Similar results are obtained when the Bamberger cleavage is carried out on (12), (24) or (25) in the presence of carbobenzoxy chloride to yield (26), (27) and (28), respectively.

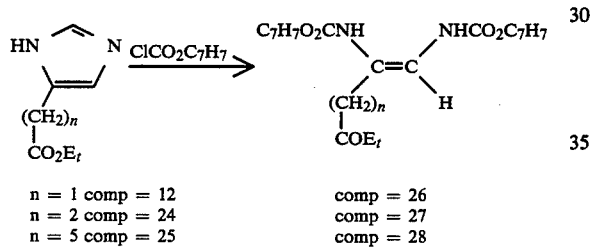

n = 1 comp = 12
n = 2 comp = 24
n = 5 comp = 25 comp = 26
comp = 27
comp = 28

For the synthesis of bifunctional EDTA derivatives with a pendant amino function, the starting materials are 4-imidazole alkylamines (29).

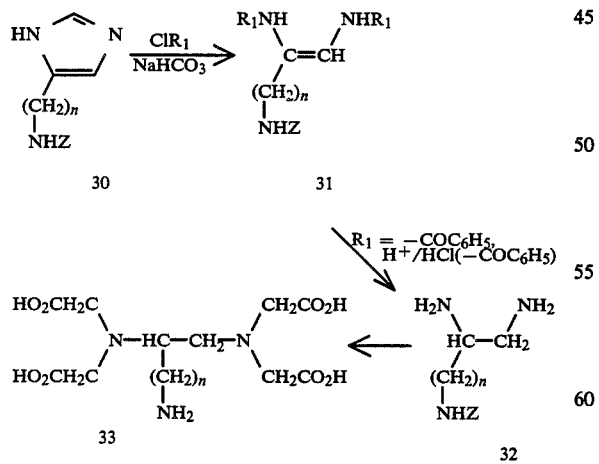

The protection of the amine function in (29) with aryl sulfonyl group (see, for example, tosylation of histidine, B. Helferich and H. Boshagne, Ber, 92, 2813 (1959), followed with the Bamberger ring cleavage of (30) in presence of benzoylchloride to yield the triamide (31).

The removal of the benzoyl group (y=COC₆H₅) from the vicinal diamine by hydrolysis, yields the expected diamines (32). Tetraalkylation of (32) and use of sodium in liquid ammonia by the method of du Vigneaud and Behrens (V. du Vigneaud and O. K. Behrens, J. Biol. Chem., 117, 27 1937) yields the EDTA analogues with a pendant amine group of type (33). Further details of the invention are given in the examples.

Substituted ethylenediamine tetraacetic acid derivatives with an aromatic side chain of type 1B can be prepared from the corresponding 2-(-phenylethyl) amino acid esters as described for substituted 1-(p-aminophenethyl)EDTA (41) are synthesized by a sequence of reactions as described in the following scheme.

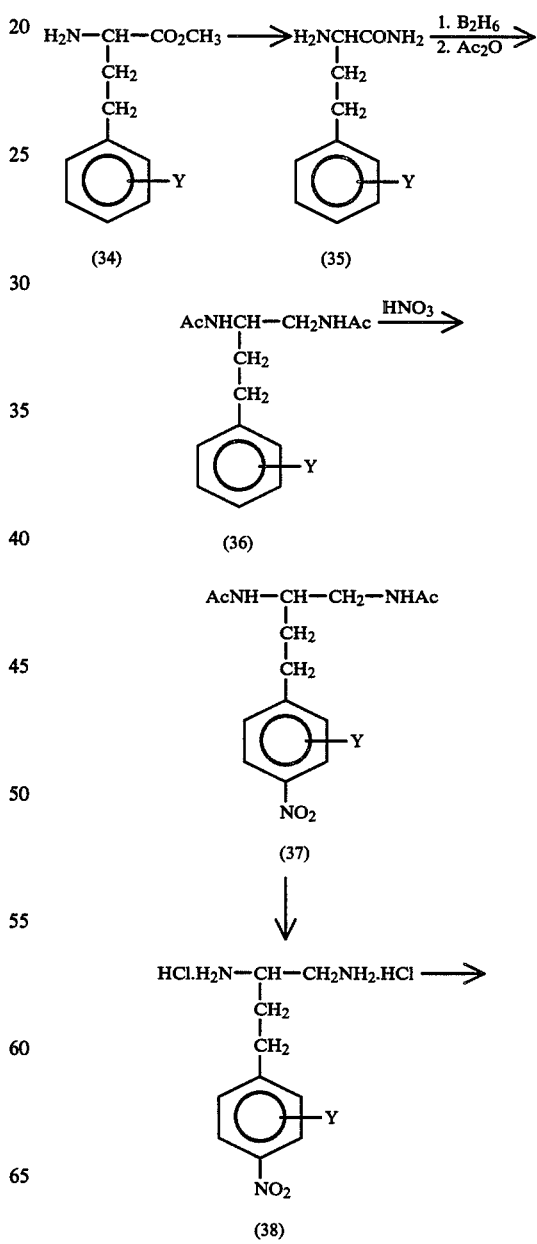

-continued

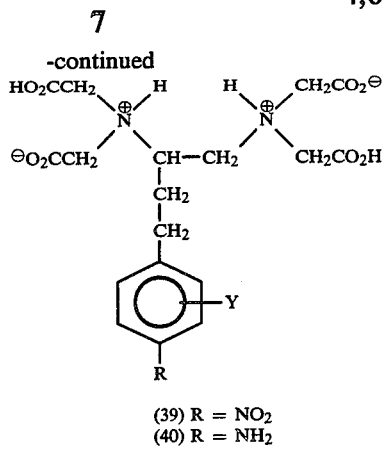

(39) R = NO$_2$
(40) R = NH$_2$

Substituted 2-amino-4-phenylbutyric acid as their methyl esters (34), which can be made by α-amidoalkylation of substituted styrenes, serve as the starting materials. The methyl esters (34) are converted through their amides (35), which are then reduced with diborane (B$_2$H$_6$) and then acetylated to afford the diacetyl amide (36). Nitration of the diacetylamide (36) occurs mainly in the para position, which usually can be obtained as a pure isomer by recrystallization. Acid hydrolysis of (37) to (38) and tetraalkylation with bromoacetic acid yield the 1-(p-nitrophenethyl) EDTA compound (39). Compound (39) is reduced to (40) only prior to conjugation to the macromolecules.

Further details of the synthetic procedure are provided in the examples.

EXAMPLES

Example 1: 4,5-diamino(N,N,N'N'-tetra-acetic acid) valeric acid

The first step is the well-known Bamberger ring cleavage-dibenzoylation of ethyl 4-imidazolepropionate (12) under Schotten-Baumann reaction conditions (PhCOCl, EtOAc-NaHCO$_3$ mixture). The dibenzoylated unsaturated chain product (13) was obtained in 82% yield, m.p. 128°–129° C., max (CHCl$_3$) 1700, 1640 cm$^{-1}$; (CDCl$_3$) 10.34 (1H, d, J 11 Hz, NH); 9.01 (1H, s, NH); 8.97–7.36 (10H, m, ArH); 6.66 (1H, d, J 11 Hz, CH); 4.16 (2H, q, J 9 Hz, OCH$_2$); 2.76–2.51 (4H, m, CH$_2$); 1.27 (3H, t, J 9 Hz, CH$_3$).

The catalytical reduction of (13) with 10% Pd in absolute ethanol in 40° C. yields ethyl 4,5-dibenzamidovalerate (14) in 91% yield, m.p. 160°–161° C., max (CHCl$_3$) 1720, 1635 cm$^{-1}$; (CDCl$_3$) 7.86–7.32 (10H, m, ArH); 4.32 (1H, t, CHN); 4.12 (2H, q, OCH$_2$); 3.63 (2H, t; CH$_2$N); 2.51 (2H, t, J 8 Hz, CH$_2$CO$_2$); 2.00 (2H, q, J 8 Hz, CH$_2$); 1.22 (3H, t, CH$_3$).

Hydrolysis of (14) in a mixture of 36% HCl-acetic acid (on 5 g of (14), 50 ml acetic acid, 120 ml 36 HCl) gives the previously unknown 4,5-diamino-valeric acid (DL- -ornithine) dihydrochloride (15) in 89% yield, m.p. 165°–170° C.; max (KBr) 2700–3100, 1680 cm$^{-1}$; (D$_2$O) 3.68 (iH, q, CHN); 3.35 (2H, d, CH$_2$N); 2.25 (2H, q, CH$_2$CO$_2$H); 2.09 (2H, t, CH$_2$).

The alkylation of (15) is performed with 5 equivalents of bromoacetic acid at pH 9.0–10.0 at 50° C. during 15 hrs. After acidification of pH 2 and evaporation of the water, the glycolic acid formed from the excess of the reagent is extracted with hot ethanol and the final product is readily isolated as the dihydrate in 40–50% yield by crystallisation from water, m.p. 182°–184° C., max (Nujol) 1740, 1720–1670 cm$^{-1}$; (D$_2$O) 3.86 (4H, s, NCH$_2$CO$_2$H); 3.72 (4H, s, NCH$_2$CO$_2^-$); 3.28–3.47 (2H, m, CH$_2$N); 2.48 (2H, t, CH$_2$CO$_2$H); 2.2–1.5 (2H, m, CH$_2$); (D$_2$O+TF) 4.20 (4H, s, NCH$_2$CO$_2$H); 3.81 (4H, s, NCH$_2$CO$_2$H); (D$_2$O+K$_2$CO$_3$) 3.61 (4H, br, s, NCH$_2$CO$_2^-$) 3.55 (2H, s, NCH$_2$CO$_2^-$); 3.50 2H, s, NCH$_2$CO$_2^-$).

Example 2: 3,4-diamino(N,N,N'N'-tetra-acetic acid) butyric acid (43)

Bamberger ring cleavage-dibenzoylation of ethyl 4-imidazoleacetate (41) under Schotten-Baumann reaction conditions (PhCOCl, EtOAc-NaHCO$_3$ mixture), yields the dibenzoylated unsaturated chain product (type 2) in 80% yield, max (CHCl$_3$) 1700, 1640 cm$^{-1}$; (CDCl$_3$) 10.31 (1H, d, J 10 Hz, NH); 9.04 (1H, s, NH); 8.90–7.39 (10H, m, ArH); 6.56 (1H, d, J 11 Hz, CH); 4.10 (2H, q, J 9 Hz, OCH$_2$); 2.75–2.50 (2H, m, CH$_2$); 1.28 (3H, t, J 9 Hz, CH$_3$).

Catalytical reduction with 10% Pd in absolute ethanol in 40° C. yields ethyl 3,4-dibenzamidoacetate in 89% yield, max (CHCl$_3$) 1720, 1635 cm$^{-1}$; (CDCl$_3$) 7.80–7.30 (10H, m, ArH); 4.33 (1H, t, CHN); 4.18 (2H, q, OCH$_2$); 3.65 (2H, t, CH$_2$N); 2.57 (2H, t, J 8 Hz, CH$_2$CO$_2$); 2.00 (2H, q, J 8 Hz, CH$_2$); 1.20 (3H, t, CH$_3$).

Hydrolysis in a mixture of 36% HCl-acetic acid (50 ml) gives 3,4-diamino-acetic acid dihydrochloride (3) in 80% yield, max (KBr) 2700–3100, 1680 cm$^{-1}$; (D$_2$O) 3.68 (1H, q, CHN); 3.35 (2H, d, CH$_2$N); 2.28 (2H, q, CH$_2$CO$_2$H); 2.19 (2H, t, CH$_2$).

Alkylation is performed with 4 equivalents of bromoacetic acid at pH 9.5–10.5 at 50° C. during 15 hrs. After acidification of pH 2 and evaporation of the water, the glycolic acid formed from the excess of the reagent is solubilized in hot ethanol and the final product is readily isolated as the dihydrate in 60% yield by crystallisation from water, max (Nujol) 1740, 1720–1670 cm$^{-1}$; (D$_2$O) 3.86 (4H, s, NCH$_2$CO$_2$H); 3.74 (4H, s, NCH$_2$CO$_2^-$); 3.38–3.47 (2H, m, CH$_2$N); 2.40 (2H, t, CH$_2$CO$_2$H); 2.2–1.5 (2H, m, CH$_2$); (D$_2$O+TF) 4.28 (4H, s, NCH$_2$CO$_2$H); 3.81 (4H, s, NCH$_2$CO$_2$H); (D$_2$O+K$_2$CO$_3$) 3.62 (4H, br, s, NCH$_2$CO$_2^-$); 3.55 (2H, s, NCH$_2$CO$_2^-$); 3.50 2H, s, NCH$_2$CO$_2^-$).

Example 3: 7,8-diamino(N,N,N'N'-tetra-acetic cid) octanoic acid (44)

Bamberger ring cleavage-dibenzoylation of ethyl 4-imidazolehexanote (42) under Schotten-Baumann reaction conditions (PhCOCl, EtOAc-NaHCO$_3$ mixture). The dibenzoylated unsaturated chain product was obtained in 70% yield, max (CHCl$_3$) 1700, 1640 cm$^{-1}$; (CDCl$_3$) 10.30 (1H, d, J 10 Hz, NH); 9.00 (1H, s, NH); 8.95–7.34 (10H, m, ArH); 6.60 (1H, d, J 11 Hz, CH); 4.16 (2H, q, J 9 Hz, OCH$_2$); 2.70–2.50 (10H, m, CH$_2$); 1.27 (3H, t, J 9 Hz, CH$_3$).

Catalytical reduction with 10% Pd in absolute ethanol in 40° C. yields ethyl 4,5-dibenzamidoctanoate in 75% yield, max (CHCl$_3$) 1720, 1635 cm$^{-1}$; (CDCl$_3$) 7.80–7.30 (10H, m, ArH); 4.30 (1H, t, CHN); 4.11 (2H, q, OCH$_2$); 3.60 (2H, t, CH$_2$N); 2.53 (2H, t, J 8 Hz, CH$_2$CO$_2$); 2.00 (10H, m, J 8 Hz, CH$_2$); 1.20 (3H, t, CH$_3$).

Hydrolysis in a mixture of 36% HCl-acetic acid (50 ml acetic acid, 120 ml 36 HCl) gives 7,8-diamino-octanoic acid dihydrochloride in 79% yield, max (KBr) 2700–3100, 1680 cm$^{-1}$; (D$_2$O) 3.68 (iH, q, CHN); 3.35 (2H, d, CH$_2$N); 2.25 (2H, q, CH$_2$CO$_2$H); 2.09 (2H, t, CH$_2$).

The alkylation is performed with 5 equivalents of bromoacetic acid at pH 9.5–10.5 at 50° C. during 15 hrs. After acidification of pH 2 and evaporation of the water, the glycolic acid formed from the excess of the reagent is solubilized in hot ethanol and the final product is readily isolated as the dihydrate in 52% yield by crystallisation from water, m.p. 182°–184° C., max (Nujol) 1740, 1720–1670 cm$^{-1}$; (D$_2$O) 3.86 (4H, s, NCH$_2$CO$_2$H); 3.72 (4H, s, NCH$_2$CO$_2^-$); 3.28–3.47 (2H, m, CH$_2$N); 2.48 (2H, t, CH$_2$CO$_2$H); 2.2–1.5 (2H, m, CH$_2$); (D$_2$O+TF) 4.20 (4H, s, NCH$_2$CO$_2$H); 3.81 (4H, s, NCH$_2$CO$_2$H); (D$_2$O+K$_2$CO$_3$) 3.61 (4H, br, s, NCH$_2$CO$_2^-$); 3.55 (2H, s, NCH$_2$CO$_2^-$); 3.50 2H, s, NCH$_2$CO$_2^-$).

Example 4: Methyl-2-amino-4-phenylbutyrate hydrochloride (34)

Dl$\alpha$-amino-$\delta$-phenylbutyric acid, prepared through amidoalkylation of styrene with methyl- -methoxyhippurate, according to Ben-Ishai et al (4.1 g, 0.018M) was dissolved in dry methanol, cooled in ice bath. Freshly distilled thionyl chloride (14.7 g, 0.12M) was added during 15 min. the ice bath was removed and the reaction mixture was left at room temp. for 3 days. Dry ether (400 ml) was added and the resulting hydrochloride ester precipitated (3.7 g, 88%) m.p. 153°–4°, lit. [D. Ben-Ishai, R. Moshenberg and J. Altman, Tetrahedron 33, 1533 (1977)] 150°–152°.

Example 5: DL-$\alpha$-amino-$\delta$-phenylbutyric acid amide (35)

The ester-hydrochloride (34) (3.7 g) was dissolved in CHCl$_3$ (200 ml) and shaken with 10% sodium carbonate solution (200 ml). The organic layer was dried (Na$_2$SO$_4$) and concentrated. The residue was transferred with a minimum volume of methanol into the pressure bottle, 20% ammonia saturated solution in dry methanol (60 ml) was added and the reaction mixture was left for 48 hrs at room temp. The solvent was removed. The crude compound (2.57 g) was crystallized from chloroformhexane (2.36 g, 82.8%) m.p. 89°–90° C. IR (CHCl$_3$) 1670 cm$^{-1}$ (CONH$_2$); NMR (CDCl$_3$) ppm; 7.38–7.13 (m, 5, aromatic); 5.7 (b, 2, CONH$_2$); 3.37 (q, 1, CH); 2.75 (t, 2, CH$_2$); 2.18–1.66 (m, 2, CH$_2$); 1.56 (s, 2, NH$_2$) The absorption bands at 5.7 and 1.56 disappeared when CD$_3$OD and TFA were added. (Found: C, 67.30; H, 7.92% N, 15.73. C$_{10}$H$_{14}$N$_2$O requires: C, 67.38; H, 7.92; N, 15.73%).

Example 6: N,N'-Diacetyl-1-phenethylethylenediamine (36)

The amide (35) (2.136 g, 0.012 mol) was dissolved in THF (100 ml, distilled from LAH) and placed in a tube 20 cm long, 4 cm wide to which a two-necked adaptor was connected. Through one neck a gas dispersion tube was inserted and attached to a borane generator. The other neck was attached to a condenser. A tube from its outlet led to a container with mercury and acetone.

After the system was washed with dry N$_2$, a slow stream of borane was bubbled through the solution (generated from NaBH$_4$ 11.3 g and boron-tri-fluoride-etherate 124 g) for 8 hrs. After addition of borane was terminated, the reaction was heated at 60° overnight. The content was transferred to a 500 ml bottle, and methanol (25 ml) was added with caution. The solvents were removed, and to the well dried residue acetonitrile (80 ml distilled over P$_2$O$_5$) triethylamine (16.4 ml) and acetic anhydride (4.9 ml) were added. The mixture was left to stand overnight at room temp. then heated under N$_2$ at 50° for 24 hrs. All solvents were evaporated, the residue dissolved in ethyl acetate and shaken with 10% sodium bicarbonate solution (15 ml). The organic layer was dried and concentrated. The product crystallized from ethyl acetatehexane (2.23 g 75%) m.p. 154°–155°. IR (CHCl$_3$) 1660 cm$^{-1}$ (COCH$_3$); NMR ppm: 7.35–7.12 (m, 5, aromatic); 6.37 (bs, 1, NH); 6.26 (d, 1, NH); 4.0 (m, 1, CH); 3.43–3.17 1 (m, 2, CH$_2$N); 2.67 (t, 2, CH$_2$); 1.94 (s, 6, CH$_3$); 1.76 (m, 2, CH$_2$). (Found: C, 67.60; H, 8.12; N, 11.38. C$_{14}$H$_{20}$N$_2$O$_2$ requires C, 67.71; H, 8.12; N, 11.29%).

Example 7: N,N'-Diacetyl-1-(p-nitrophenethyle)ethylenediamine (37)

Compound (36) (2.4 g 9.4 mmol) was added in small portions into 95% HNO$_3$ and stirred for 3 hrs at −40° C. The cold nitration mixture was poured into crushed ice-solid Na$_2$CO$_3$ mixture and extracted with ethyl acetate. The crude compound (2.75 g, 99%) obtained after evaporation of solvent, had a m.p. 138°–145° C. and its H NMR spectrum showed a well formed A$_2$B$_2$ system indicating that the ortho isomer, if present, does not exceed 10%. Crystallization from acetone-hexane gave pure para isomer (1.13 g, 41%) m.p. 172°–173°. IR (CHCl$_3$): 1660 cm$^{-1}$ (NHCOCH$_3$); 1350$^{-1}$ (NO$_2$). NMR (CDCl$_3$) ppm: 8.19 and 8.08; 7.48 and 7.37 (A$_2$B$_2$) Q, 4, aromatic); 6.3 (b, 2, NH); 4.0 (m, 1, CH); 3.3 (m, 2, CH$_2$N); 2.8 (m, 2, CH$_2$); 1.98 (s, 6, CH$_3$); 1.86 (m, 2, CH$_2$). (Found: C, 56.70; H, 6.40; N, 13.85. C$_{14}$H$_{19}$N$_3$O$_4$ requires C, 57.1; H, 6.48; N, 14.28%)>

After evaporation of the mother liquid from cristalliation, 1.62 g was obtained, now enriched in the ortho isomer, roughly estimated at 20% by the PMR of the aromatic region. Further crystallization from this mixture yields more para isomer.

Example 8: 1-(p-Nitrophenethyl)ethylenediamine dihydrochloride (38)

Diacetyl (37) (588 mg, 2 mmol) was refluxed in a mixture of acetic acid (3 ml) and conc. HCl (4.5 ml) for 20 hrs. The solvents were evaporated and the residue was dissolved in absolute alcohol and precipitated with ether. The hygroscopic hydrochloride was obtained quantitatively. NMR (D$_2$O) ppm: 8.24 and 8.13; 7.54 and 7.43 (A$_2$B$_2$ Q, 4, aromatic); 3.78–3.55 (m, 1, CH); 3.43–3.35 (m, 2, CH$_2$N); 3.03–2.83 (m, 2, CH$_2$); 2.26–1.96 (m, 2, CH$_2$). (Found: Cl, 24.00; N, 13.84. C$_{10}$H$_{17}$Cl$_2$N$_3$O$_2$.H$_2$O requires Cl, 23.61; N, 13.99%).

Example 9: 1-(p-Nitrophenethyl)ethylenediaminetetraacetic acid (39)

All glassware used in this experiment was washed in doubly distilled water. Dihydrochloride ( . . . ) (430 mg, 1.43 mmol) dissolved in water (2 ml) and neutralized to pH 7 with 1N KOH in three-necked flask in which a glass electrode was immersed, was mixed with bromacetic acid (1 g, 7 mM) previously neutralized to pH 7 with 6N KOH and 1N KOH towards the end. The mixture was brought to pH 10.5 with 6N KOH and then heated in 50° C. bath. The pH of the reaction was kept between 9.5–10.5. Absorption of alkali was fast during the first hour and was terminated after 4.5 hrs. The reaction was left at 50° C. overnight, cooled in an ice-bath and acidified with 6N HCl. The product precipitated between pH 4–2.5. The mother liquid was decanted and the tetraacid was crystallized from double distilled water. (467 mg. 71%), m.p. 188°–189°. IR (KBr); 1660–1710 cm$^{-1}$ ($CO_2$ and $CO_2H$); 1330 cm$^{-1}$ ($NO_2$) NMR ($D_2O+K_2CO_3$) ppm: 8.22 and 8.11; 7.49 and 7.38 ($A_2B_2$ Q, aromatic); (Found: C, 47.15; H, 5.40 N, 9.17, $C_{18}H_{23}N_3O_{10}$. $H_2O$ requires C, 47.06; H, 5.49; N, 9.17%).

Example 10:
1-(p-Aminophenethyl)ethylenediaminetetraacetic acid (40)

Tetraacid (39) (94.4 mg, 0.22 mmol) was dissolved in absolute ethanol, (5 ml) triethylamine (200 μl) and 10% Pd on charcoal (30 mg) were added. The mixture was hydrogenated under 1 atm. of hydrogen overnight at room temp., filtered, evaporated and dried in high vacuum. According to NMR it is a salt containing two equivalents of triethylamine. NMR ($D_2O$) ppm: 7.29–7.02 (m, 4, aromatic); 3.72 (s, 2, COC$\underline{H_2}$N); 3.65 (s, 6, COC$\underline{H_2}$N); 3.19 (q. 14, C$\underline{H_3CH_2}$N and s, C$\underline{H}$C$\underline{H_2}$N); 1.28 (t, 18, C$\underline{H_2}$).

After some KOH was added, the sample was evaporated to dryness and the NMR spectrum was repeated in $D_2O$ The aromatic region now exhibited a well formed quartet of the AA'BB' system: 7.98 and 7.88 (d, 2, aromatic); 6.85 and 6.75 (d, 2, aromatic); 3.34 (s, 2 COC$\underline{H_2}$N); 3.20 (s, 6, COC$\underline{H_2}$N); 2.80 (bs, 2. C$\underline{H_2}$N) Rf=0.54 on silica TLC using EtOH-25% $NH_4OH$ (4:1) as eluent.

Example 11: $N^{Im}$,N-Ditosylhistamine (41)

The tosyaltion procedure is the adaptation of the Helferich and Boshagen method applied for hisdine methyl, ester (B. Helferich and H. Boshagen, Ber, 92, 2813, 1959)

Histamine dihydrochloride (3.68 mg, 0.02M) was dissolved in chloroform (400 ml). Triethylamine (16.1 g. 160. mM) was added. To the mixture, cooled in an ice-bath, p-toluene sulfonyl chloride (7.62 g, 0.04 mM) was added. The reaction was left for 2 hrs at 10° C. and then overnight at room temperature. Chloroform was evaporated, and ethylacetate (250 ml) added. Triethylamine hydrochloride was filtered, the solution concentrated and the residue crystallized from ethyl acetatehexane, m.p. 135°–6° (6.2 g, 74%). IR (CHCl$_3$) 1150 and 1070 cm$^{-1}$ (SO$_2$). NMR (CD$_3$OD) 7.70 and 7.34; (8H, A$_2$B$_2$, q, J 11 Hz, ArH); 7.54 and 6.78 (2H, 2s, Im); 3.27–3.17 (2H, m, CH$_2$); 3.09–2.78 (2H, m, CH$_2$); 2.78 (6H, s, CH$_3$); (CDCl$_3$) 7.85–6.98 (1CH, two separate A$_2$B$_2$ patterns of ArH and Im); 5.58 (1H, t, J 8 Hz, NH); 3.30–3.08 (2H, q, CH$_2$); 2.63 (2H, t, CH$_2$); 2.43 (3H, s, CH$_3$); 2.40 (3H, s, CH$_3$). Found: C, 54.49; H, 5.20; N, 9.73; C$_{19}$H$_{21}$N$_3$O$_4$S$_2$ requires C, 54.41; H, 5.05; N, 10.02%).

Example 12: N-Tosylhistamine (42)

A. Distosylhistamine (41) (4.19 g, 0.01 mM) was dissolved in ethanol (400 ml) and mixed with the solution of sodium carbonate (4.24 g in 250 ml). The reaction mixture was stirred at room temperature for 24 hrs, then heated at 60° C. for 2 hrs. Ethanol was evaporated and the water solution extracted six times with chloroform. The organic layter was washed with water, dried (Na$_2$SO$_4$) and concentrated. The residue was recrystallized from ethyl acetatehexane yielding 1.4 g, 53% of product. m.p. 150–151. IR (CHCl$_3$) 1150 cm$^{-1}$ (SO$_2$). NMR (CD$_3$OD) 7.60 and 7.35 (4H, A$_2$B$_2$, q, ArH); 7.55 and 6.79 (2H, 2s, Im); 3.19–3.08 (2H, m, CH$_2$); 2.70–2.61 (2H, m, CH$_2$); 2.41 (3H, s, CH$_3$); Found: C, 54.08; H, 5.76; N, 15.38; C$_{12}$H$_{15}$N$_3$O$_2$S requires C, 54.33; H, 5.70; N, 15.84%).

B. The removal of $N^{Im}$ tosyl group was also performed by stirring ditosylhistamine (41) (4.19 g) in ethanol (300 ml)-25% NH$_4$OH (250 ml) mixture 12 hrs at room temp, and 3 hrs at 60° C. After evaporation of the solvents, the crude product was dissolved in a small volume of methanol, mixed with silica gel (woelm, 50 g) dried, and introduced into the column. Elution with ethyl acetate-5% methanol gave the pure tosylhistamine 1.57 g, 60%. The same reaction at 100° C. in an autoclave gave 100% yield.

C. $N^{Im}$-Tosyl group was also removed by transacylation procedure with acetic anhydride and pyridine, followed by methanolysis (J. M. van der Eijk, R. J. M. Nolte and J. W. Zwikker, J. Org. Chem. 45, 547, 1980).

Example 13: 3,4-Dibenzamidobut-3-enetosylamine (43)

Tosylhistamine (1.06 g, 4 mM) was suspended in ethyl acetate (200 ml) in a three necked bottle and stirred for 30 min at room temperature to get a fine suspension, then cooled in an ice bath. Benzoyl chloride (5.2 g) dissolved in ethyl acetate (100 ml) and 1M NaHCO$_3$ (120 ml) was added simultaneously from two dropping funnels, upon cooling during 4 h. Care was taken to keep the pH of the mixture basic. The vigorous stirring was continued overnight at room temperature. The organic layer was separated and concentrated. The residue was redissolved in THF (150 ml) and vigorously stirred with 10% NaHCO$_3$ (300 ml) for 6 days. THF was evaporated, the water layer extracted three times with ethyl acetate, concentrated and filtered through silica gel column (40 g) using ethyl acetate-hexane (7:3) as eluent. 1.25 g 67% of the Bamberger-ring-opened product was obtained. After recrystallisation (ethyl acetate-hexane) 1.01 g. 53% of (43) m.p. 151°–2° C. IR (CHCl$_3$) 3000–3400 m (NH), 1700 sh, w, 1650 s cm$^{-1}$ CON. NMR (CDCl$_3$); 8.16 (1H, d, J 12 Hz, NH); 7.98 (1H, s, NH); 7.91–7.17 (14H, m, ArH); 6.61 (1H, d, J 12 Hz, CH); 5.61 (1H, t, NHSO$_2$); 3.15–3.08 (2H, m, CH$_2$N); 2.52 (2H, t, J 8 Hz, CH$_2$); 2.36 (3H, s, CH$_3$).

When D$_2$O and TFA (trifluoroacetic acid) were added, the signals of NH at 8.16, 7.98 and 5.63 disappeared; the signal at the olefinic proton at 6.61 became a singlet, and the multiplet at 3.12 became a triplet. (Found: C, 64.77; H, 5.40; N, 9.15; C$_{25}$H$_{25}$N$_3$O$_4$S requires C, 64.78; H, 5.44; N, 9.06%).

If the treatment of the crude reaction product with THF-NaHCO$_3$ solution is shortened to several hours (1N-benzoyl)-3,4-dibenzamidobutene tosylamine (44) is isolated as the main product. Tribenzoylated product is eluted from the silica column with ethyl acetate-hexane before the dibenzoyl. It crystallizes from ethyl acetate-hexane with 1.5 molecule of water (62% yield (44). IR (CHCl$_3$) 3200–3400 w (NH); 1680 sh, 1650 s (CON) NMR (CDCl$_3$) 9.97 (1H, d, J 12 Hz, NH); 9.11 (1H, s, NH); 8.04–7.36 (19H, m, ArH); 6.56 (1H, d, J 12 Hz, CH); 3.65 (2H, t, J 9 Hz, CH$_2$); 2.47 (3H, s, CH$_3$) superimposed with 2.43 (2H, t, J 9 Hz, CH$_2$); 1.25 (s, H$_2$O). Found: C, 64.36; H, 5.17; N, 7.58; C$_{32}$H$_{30}$N$_3$O$_5$S requires C, 64.64; H, 5.38; N, 7.42%).

The tribenzoyl is transformed to the dibenzoyl and benzamide with alcoholic ammonia solution.

Example 14: 3,4-Dibenzamidobutyl tosylamine (45)

The unsaturated dibenzoyl (1.013 g) was hydrogenated for 20 h in Parr Apparatus in ethanol (200 ml) in the presence of 10% Pd on charcoal (400 mg) with external heating using a lamp. The product tends to crystallize in the apparatus. It was redissolved, filtered concentrated and crystallized from ethanol. m.p. 228°–9° C. (45). NMR (CD$_3$OD) 7.80–7.32 (14H, m, ArH); 3.73 (2H, d, CH$_2$NC); 3.10 (2H, m, CH$_2$NS); 2.34 (3H, s, CH$_3$); 1.90 (2H, m, CH$_2$).

Conjugation of the bifunctional chelating agents to macromolecules

The conjugation of the bifunctional chelating agents described above through their amine terminal, can be accomplished by methods very well known in quantitative enzyme immunoassay (Eiji Ishikawa, Enzyme labelling of antigens and antibodies for quantitative enzyme immunoassay, 1980).

A bifunctional coupling agent which can bind the amino function of the bifunctional chelating agent on one hand, and the free amine or thiol of a protein on the other, is usually applied. Thus, Ishikawa, in his review, describes cyanuric chloride, 4,4'-difluro-3,3-dinitrodiphenylsulfone, toluene-2,4-diisocyanate, N,N'-dicyclohexylcarbodiimide, Bis-diazotized o-dianisidine, glutaraldehyde and bis(glutaraldehyde), maleimide, maleimide ester and dimaleimide ester. Pyridyl disulfide, S-acetylmercapto succinic anhydride, o-phenylenedimaleimide, N,N'-oxydimethylene dimaleimide, N-hydroxysuccinimide ester of m-maleimidobenzoic acid, N-hydroxysuccinimide ester of N-(4-carboxycyclohexylmethyl) maleimide, N-hydroxysuccinimide ester of N-(4-carboxyphenylmethyl) maleimide, N-hydroxysuccinimiide ester of iodoacetic acid, N-hydroxysuccinimide ester of 3-(2'-pyridyldithio) propionic acid, methyl 3-(4'-dithiopyridyl propionimidate, methyl 3-mercapto propionimidate, methyl 4-mercaptobutyrimidate, 2-iminothiolane and p-benzoquinone.

In addition to the reagents described above, there are offered, commercially, a large number of bifunctional crosslinking reagents (Pierce Handbook and General Catalogue, 1981-2, pp. 162–166). These are listed below:

(1) Bifunctional imidoesters
  (a) Non cleavable: dimethyladipimidate 2HCl, dimethyl pimelimidate 2HCl, dimethylsuberimidate.
  (b) Cleavable by thiols: dimethyl 3,3'-dithio-bispropionimidate 2HCl, 2-iminothiolane HCl.
(2) Bifunctional N-hydroxysuccinyl esters: Disuccinimidyl suberate, bis-[2-(succinimidoxy-carbonyloxy)]sulfone, disuccinimidyl (N,N'-diacetylhomocystine), disuccinimidyl tartarate, dithio bis(-succinimidyl propionate), ethylene glycol bis(succinimidyl succinate).
(3) Heterobifunctional reagents:
  (a) Cleavable: p-azidophenacyl bromide, p-azidophenyl glyoxal, (2-p-Nitrophenyl)alkyl-4-nitro-3-carboxyphenylsulfide, 4-fluro-3-nitrophenylazide, N-hydroxy succinimidyl-4-azido benzoate, m-maleimidobenzoyl N-bydroxysuccinimide ester, methyl-4-azidobenzo imidate HCl, p-nitrophenyl-2-diazo-3,3,3,-trifluro propionate, N-succinimidyl-6 (4'-azido-2'-nitro phenylamino hexanoate), succinimidyl 4-(N-maleimidoethyl)cyclohexane-1-carboxylate, succinimidyl-4(p-maleimidophenyl) butyrate.
  (b) Cleavable: N-succinimidyl (4-azidophenyldithio) propionate, N-succinimidyl 3-(2-pyridyldithio) propionate.
(4) Homobifunctional Reagents:
  (a) Non-cleavable: 1.5-difluro-2,4-dinitrobenzene, 4,4'-difluro-3,3'-dinitrodiphenylsulfone, 4,4'-diisothiocyana-2,2'-disulfonic acid stilbene, p-phenylene diisothiocyanate.
  (b) Cleavable: carboxyl bis(L-mehionine p-nitrophenyl ester), 4,4'-dithiobisphenylazide, erythritol bis carbonate.

In addition to the array of reagents discussed above, other specific methods such as the use of Avidin-Biotin interaction can be used (see J. L. Guesdon, T. Ternynck and S. Avrameas, J. of Histochemistry and cytochemistry, 27, 1131 (1979).

It is obvious that for this wide range of conjugation methods, there is no need to specify a priory the exact binding method, since this will be decided by considering the chemical properties of each macromolecular conjugation candidate.

Conjugation to hormones and other haptens

As with proteins and enzymes, there are several methods which were developed to activate haptenes such as steroidal hormones, in order to bind them to proteins, and their use in radioimmunoassay (D. I. Chapman, Chem. in Britain, 439–447, 1979). F. Kohen, S. Bauminger and H. R. Lindner (Steroid immunoassay, Proceedings of the 5th Tenovus Workshop, Cardiff, April 1974, E. H. D. Cameron, S. G. Hillier and K. Griffiths, pp. 11–31) have described in detail, preparation of antigenic steroid-protein conjugates, usually through the synthesis of pendant alkanoic acid derivatives of the steroids, e.g. by esterification - hydroxy function in progesterone with - -alkanedicarboxylic acid, or by oximation of 20- -dihydroprogesterone-3-(O-carboxymethyl)oxime, with (O-carboxymethyl) hydroxylamine HCl, or by thiolation of $^4$-3-ketosteroids with -thioalkanoic acids. All the derivatives described above and others described in the original publication can be used to couple the bifunctional chelating agents of this invention through their amine terminal to the carboxyl terminal of the modified steroid derivative.

Further details on steroid modification and coupling to proteins are found in D. K. Kirk, Terpenoids and Steroids, Vol. 9, The Chemical Society, a specialist periodical publication, pp. 255–331.

We claim:
1. A conjugate of the formula:

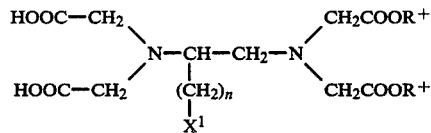

wherein $X^1$ is selected from the group consisting of —COO, —NH, —CHO, —CH=N,

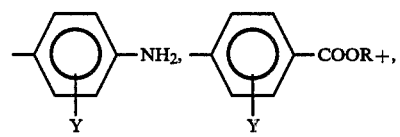

—COOAlk, —COOBenzyl, —COOAralkyl, wherein n is an integer of from 1 to 20;

wherein alkyl is a straight or branched chain alkyl group of from 1 to 20 carbon atoms, aralkyl is an aryl group substituted with a straight or branched chain alkyl group of from 1 to 20 carbon atoms, Y is selected from the group consisting of alkyl, cycloalkyl, aryl, and non-interfering substitutes, wherein cycloalkyl is a cyclic alkyl group of from 3 to 8 carbon atoms;

Q is a hapten selected from the group consisting of hormones, steroids, enzymes, and proteins, and Q is convalently bound to the $X^1$ group.

2. A complex of the conjugate of claim 1, of the formula:

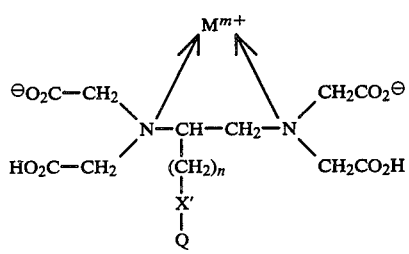

wherein:

(a) X' is selected from —COOH, —NH$_2$, —CHO, —CH=N, and n=1 to 20; and

X' is selected from

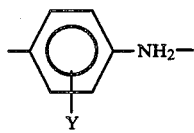

wherein n is an integer of 2 to 20,

Y is selected from alkyl, cycloalkyl, aryl, or a non-interfering substitutent, where alkyl is a straight or branched alkyl group of from 1 to 20 carbon atoms, cycloalkyl is a cycloalkyl group of from 3 to 8 carbon atoms;

wherein $M^{m+}$ is a chelatable metal cation isotope with a short half-life, selected from the group consisting of gallium 67, indium-111, technetium-99m and scandium-47; Q is a hapten selected from the group consisting of hormones, steroids proteins and enzymes, and where Q is covalently bound to MR- through the X group, and where the metal ion is chelated by the ethylendiaminetetraacetic acid group.

3. An immunoassay technique which comprises coupling a bifunctional chelating agent defined in claim 1 to a molecule selected from the group consisting of haptens, steroids, proteins, and enzymes, and adding it to the analyte prior to determination, followed by equilibration with a suitable radio tracer with a short lifetime, selected from the group consisting of gallium-67, indium 111, technetium-99m, gallium-68 and scandium-47, separating the complex metalchelating agent-macromolecular conjugate, and determining the metal content.

4. A process for determination of biological analytes of the type QH, wherein Q is a hapten selected from the group consisting of hormones, steroids, proteins, and enzymes, comprising adding a bifunctional chelating agent of the type R-A to the analyte, wherein R is

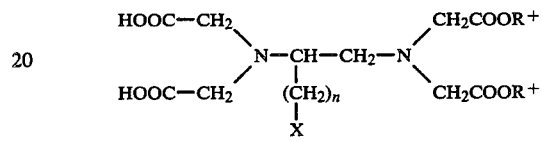

wherein X is selected from the group consisting of —coor+, —NH$_2$, —CHO, —CH=N, —COORALK, —COO—benzyl, —COO—aralkyl,

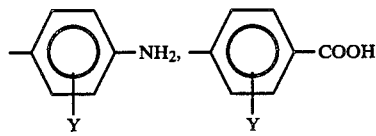

n=1 to 20

Y is selected from the group consisting of alkyl, cycloalkyl, aryl, wherein alkyl is a straight or benched alkyl group of from 1 to 20 carbon atoms, cycloalkyl is a cycloalkyl group of from 3 to 8 carbon atoms, aralkyl is selected from the group consisting of aryl groups substituted with straight or branched chain carbon atoms having from 1 to 20 carbon atoms;

equalibrating the bifunctional chelating agent with a chelatable metal ion $M^{m+}$, wherein $M^{m+}$ is a chelatable metal cation isotope with a short halflife selected from the group consisting of gallium-67, indium-111, technetium-99 m, galluim-68, and scanduim-47, forming the metal complx R-X-Q-M;

separating QH and R-X-Q-M from excess free metal ions;

determining the bound metal ion by a suitable counting method; and calculating the concentration of analyte QH.

* * * * *